(12) United States Patent
Mukai et al.

(10) Patent No.: US 10,799,391 B2
(45) Date of Patent: Oct. 13, 2020

(54) SCROTAL SHEET

(71) Applicant: Mitsuboshi Product Planning Co., Ltd., Tokyo (JP)

(72) Inventors: Toru Mukai, Tokyo (JP); Nobuaki Miyata, Tokyo (JP); Hiroshi Okada, Koshigaya (JP)

(73) Assignee: Mitsuboshi Product Planning Co., Ltd., Tokyo (JP)

( * ) Notice: Subject to any disclaimer, the term of this patent is extended or adjusted under 35 U.S.C. 154(b) by 5 days.

(21) Appl. No.: 16/073,895

(22) PCT Filed: Jan. 6, 2017

(86) PCT No.: PCT/JP2017/000196
§ 371 (c)(1),
(2) Date: Jul. 30, 2018

(87) PCT Pub. No.: WO2017/134977
PCT Pub. Date: Aug. 10, 2017

(65) Prior Publication Data
US 2019/0038457 A1   Feb. 7, 2019

(30) Foreign Application Priority Data

Feb. 5, 2016   (JP) .................................. 2016-021250

(51) Int. Cl.
*A61F 7/02*   (2006.01)
*A61F 7/03*   (2006.01)
(Continued)

(52) U.S. Cl.
CPC ................ *A61F 7/03* (2013.01); *A01N 37/40* (2013.01); *A61F 7/02* (2013.01); *A61K 31/045* (2013.01);
(Continued)

(58) Field of Classification Search
CPC .... A61F 7/02; A61F 7/106; A61F 2007/0048; A61F 2007/0244; A61F 2007/026;
(Continued)

(56) References Cited

U.S. PATENT DOCUMENTS

| 4,253,464 A | 3/1981 | Zorgniotti et al. |
| 5,409,500 A * | 4/1995 | Dyrek ........................ A61F 7/10 607/111 |

(Continued)

FOREIGN PATENT DOCUMENTS

| CN | 202526407 U | 11/2012 |
| CN | 203400241 U | 1/2014 |

(Continued)

OTHER PUBLICATIONS

International Search Report; issued in PCT/JP2017/000196; dated Apr. 4, 2017.

(Continued)

*Primary Examiner* — Eun Hwa Kim
*Assistant Examiner* — Adam Z Minchella
(74) *Attorney, Agent, or Firm* — Studebaker & Brackett PC

(57) ABSTRACT

A scrotal sheet includes a paste/water-retaining material layer containing at least moisture and a cooling material that uses vaporization heat resulting from evaporation of the moisture, a surface material layer on a surface of the paste/water-retaining material layer, and a notch configured to from a three-dimensional shape to surround the scrotum when the scrotal sheet is used.

8 Claims, 7 Drawing Sheets

(51) Int. Cl.
*A01N 37/40* (2006.01)
*A61K 31/045* (2006.01)
*A61F 7/00* (2006.01)

(52) U.S. Cl.
CPC ............... *A61F 2007/0048* (2013.01); *A61F 2007/0263* (2013.01); *A61F 2007/0266* (2013.01)

(58) Field of Classification Search
CPC ........ A61F 2007/0226; A61F 2007/0201–038; A61F 7/03; A61F 2007/0263; A61F 2007/0266; A61F 7/08; A61F 2007/0058; A41D 13/0056; A41D 13/0525; A41B 9/023; A01N 37/40; A61K 31/045
See application file for complete search history.

(56) References Cited

U.S. PATENT DOCUMENTS

| | | | | |
|---|---|---|---|---|
| 6,723,115 | B1* | 4/2004 | Daly | A61F 7/02 607/108 |
| 2004/0244413 | A1* | 12/2004 | Trinh | A61F 7/103 62/530 |
| 2010/0137953 | A1* | 6/2010 | Stein | A61B 5/103 607/112 |
| 2013/0331917 | A1* | 12/2013 | Margolis | A61F 7/10 607/108 |
| 2013/0338742 | A1 | 12/2013 | Gallen et al. | |
| 2015/0157493 | A1 | 6/2015 | Agha | |
| 2016/0331048 | A1* | 11/2016 | Runcie | A41D 13/0537 |

FOREIGN PATENT DOCUMENTS

| | | |
|---|---|---|
| JP | 36-025599 Y1 | 9/1961 |
| JP | S57-148944 A | 9/1982 |
| JP | 62-15328 U | 1/1987 |
| JP | 3031041 U | 11/1996 |
| JP | 2001-299807 A | 10/2001 |
| JP | 3083311 U | 1/2002 |
| JP | 3166764 U | 3/2011 |
| KR | 1020020071121 A | 9/2002 |
| TW | M495095 U | 2/2015 |
| WO | 02/47589 A1 | 6/2002 |
| WO | 2010/039277 A1 | 4/2010 |

OTHER PUBLICATIONS

Written Opinion; issued in PCT/JP2017/000196; dated Apr. 4, 2017.
Notification of the First Office Action issued by the State Intellectual Property Office of the People's Republic of China dated Mar. 26, 2018, which corresponds to Chinese Patent Application No. 201780001005.8.
Notification of the Second Office Action issued by the State Intellectual Property Office of the People's Republic of China dated Jul. 11, 2018, which corresponds to Chinese Patent Application No. 201780001005.8.
Web site of product page on Babystart Ltd.; https://babystart.co.uk/feritilmate/.
http://www.baike.com/wiki/.
An Office Action mailed by the Korean Intellectual Property Office dated May 23, 2019, which corresponds to Korean Patent Application No. 10-2018-7021949 and is related to U.S. Appl. No. 16/073,895.
International Search Report issued in PCT/JP2019/016639; dated Jun. 4, 2019.
The extended European search report issued by the European Patent Office dated Aug. 16, 2019, which corresponds to European Patent Application No. 17747141.4-1111 and is related to U.S. Appl. No. 16/073,895.
Waseem Osman M et al: "A study of the effect of the FertiMate™ scrotum cooling patch on male fertility . SCOP trial (scrotal cooling patch) study protocol for a randomised controlled trial", Trials, Biomed Central, vol. 13, No. 1, Apr. 27, 2012, 3 pages, London, GB.

* cited by examiner

SCROTAL SHEET

CROSS-REFERENCE TO RELATED APPLICATION

This application is based upon and claims the benefit of priority from Japanese Patent Application No. 2016-021250 filed to the Japan Patent Office on Feb. 5, 2016, the entire disclosure of which is incorporated herein by reference.

Technical Field

The present disclosure relates to an improvement in reduction or degradation in mobility of sperm, idiopathic oligospermia or the like as a cause of male infertility and, in particular, to a scrotal sheet used to be attached to the scrotum during use.

Background Art

Conventionally, patients have performed countermeasures such as attaching a Babystart patch (FertilMate Cooling Patch (product name)) to improve idiopathic oligospermia or the like. The patch is formed into a rectangular shape in a plan view (see Non Patent Literature 1: Web site of FertilMate product page of Babystart Ltd. (babystart-.co.uk)).

SUMMARY

However, the patch disclosed in the above Non Patent Literature 1 is angulated at its four corners in a plan view. Therefore, when the patch is attached to the scrotum, a gap may be formed between the patch and the scrotum or bent parts formed at the four corners contact an underwear. Accordingly, since the patch is easily peeled off from the scrotum and poorly adheres to the scrotum, the patch is not suitable for attachment to the scrotum.

An object of the present disclosure is to provide a scrotal sheet that can improve its adhesion to the scrotum when attached to the scrotum compared to a conventional art.

In order to achieve the above object, a scrotal sheet according to the present disclosure includes: a paste/water-retaining material layer containing at least moisture and a cooling material that uses vaporization heat resulting from evaporation of the moisture; a surface material layer on one surface of the paste/water-retaining material layer; and notches configured to from a three-dimensional shape to surround the scrotum when the scrotal sheet is used.

DETAILED DESCRIPTION

Hereinafter, the present disclosure will be described with reference to the drawings showing embodiments of the present disclosure.

Figure 1:
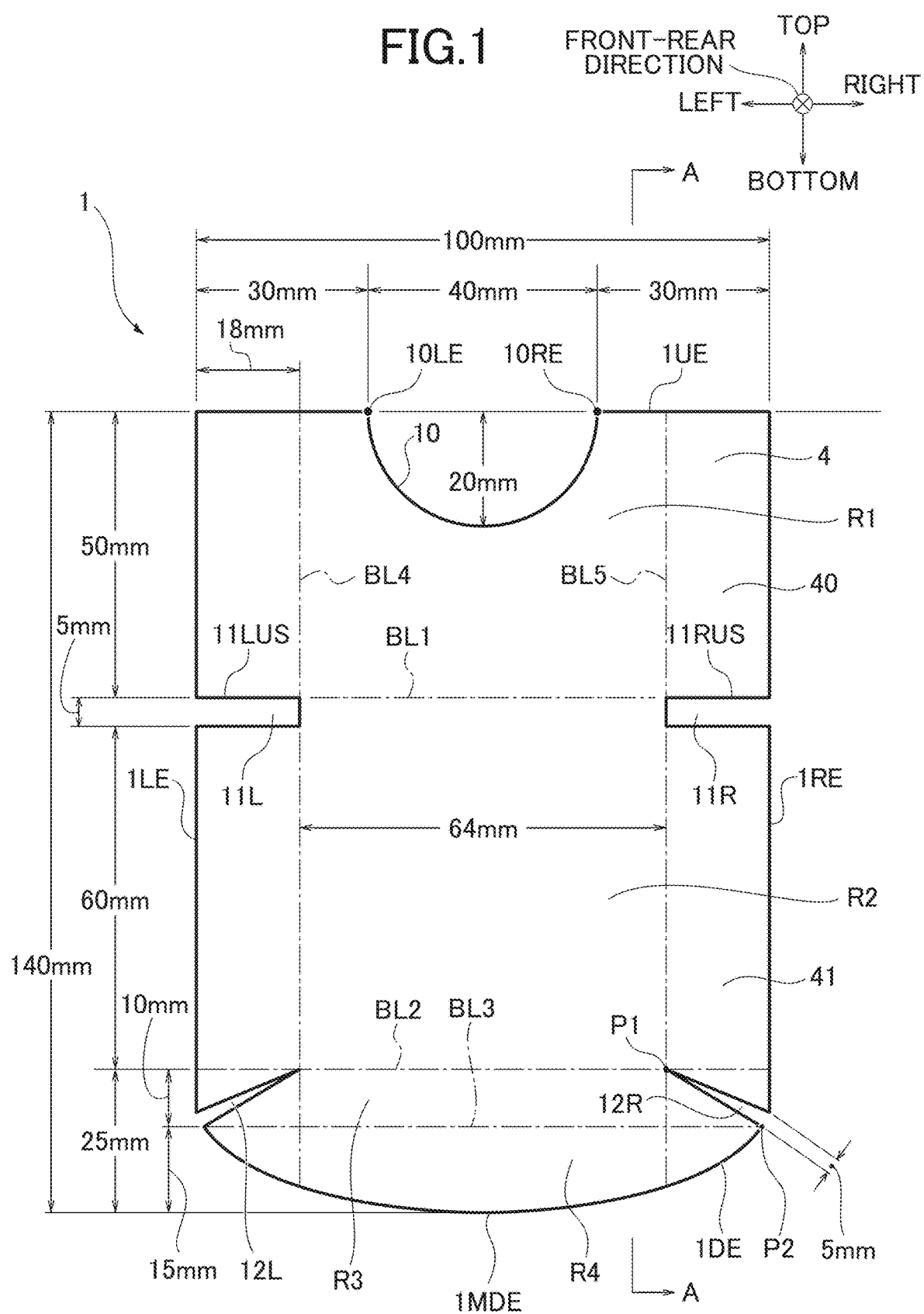
FIG. 1 is a plan view showing an example of the whole shape of a scrotal sheet 1.
Figure 2:
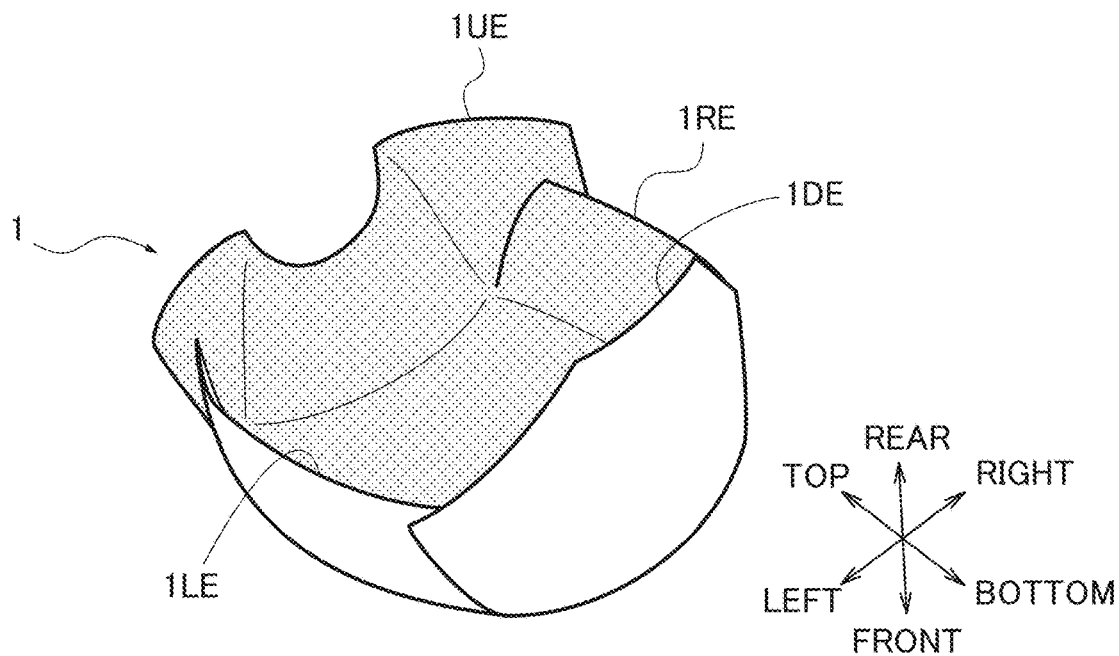
FIG. 2 is a perspective view showing a state in which the scrotal sheet 1 is being bent backward.

(Whole Shape of Scrotal Sheet) FIG. 1 is a plan view showing an example of the whole shape of a scrotal sheet 1. FIG. 2 is a perspective view showing a state in which the scrotal sheet 1 is being bent backward.

As shown in FIG. 1, the scrotal sheet 1 has an elongated shape elongated in one direction as a whole.

Note that in the following description, a right-left direction, a front-back direction, a top-bottom direction, or the like will represent each direction of the scrotal sheet 1.

The scrotal sheet 1 is a sheet that surrounds the scrotum in a three-dimensional shape when the scrotal sheet is used. Specifically, as shown in FIG. 2, the scrotal sheet 1 is bent backward along five bend lines BL1 to BL5 to be arranged in a three-dimensional shape when attached to the scrotum. The scrotal sheet 1 is divided into a plurality of regions by the bend lines BL1 to BL5 shown by dashed lines in the figure. Note that the bend line BL1 functions also as a cut line for dividing a surface protection film 4 into a plurality of portions 40 and 41. In the present embodiment, the bend lines BL1 to BL3 are three straight lines by which the scrotal sheet 1 is divided into four portions in the top-bottom direction, and the bend lines BL4 and BL5 are two straight lines by which the scrotal sheet 1 is divided into three portions in the right-left direction.

A distance in the top-bottom direction from an upper end 1UE to the bend line BL1 of the scrotal sheet 1 is preferably 35 to 60 mm, a distance in the top-bottom direction from the bend line BL1 to the bend line BL2 is preferably 50 to 65 mm, and a distance in the top-bottom direction from the bend line BL2 to the bend line BL3 is preferably 5 to 20 mm. In addition, a distance in the right-left direction from a left end 1LE to the bend line BL4 is preferably 10 to 20 mm, a distance in the right-left direction from the bend line BL4 to the bend line BL5 is preferably 50 to 65 mm, and a distance in the right-left direction from the bend line BL5 to a right end 1RE is preferably 10 to 20 mm.

As shown in FIG. 1, the scrotal sheet 1 has a shape elongated in the top-bottom direction in a plan view. Here, in the scrotal sheet 1, the "elongated" represents that a long side (140 mm in the present embodiment) extending in the top-bottom direction is longer than a short side (100 mm in the present embodiment) extending in the right-left direction.

(Configuration of Notch) The scrotal sheet 1 includes a plurality of notches configured to from a three-dimensional shape to surround the scrotum when the scrotal sheet is used.

(Configuration of Notch 10) At least one of the notches is a notch formed at one end to cause a penis to pass therethrough. In the present embodiment, a notch shown by a reference numeral 10 is formed at the upper end 1UE as shown in FIG. 1. The notch 10 is formed at a central part in the right-left direction at the upper end 1UE of the scrotal sheet 1.

The notch 10 has a semicircular shape in a plan view. The size of the notch 10 is set so that its radius is preferably 15 to 25 mm, and that its opening length is preferably 15 to 25 mm.

In addition, a distance in the right-left direction from a left end 10LE of the notch 10 to a left end 1LE of the scrotal sheet 1 is preferably 25 to 35 mm. Similarly, a distance in the right-left direction from a right end 10RE of the notch 10 to a right end 1RE of the scrotal sheet 1 is preferably 25 to 35 mm.

(Configurations of Notches 11L, 11R, 12L, and 12R) Notches 11L and 12L are formed at the left end 1LE as shown in FIG. 1 and used to bend and raise the left end 1LE as shown in FIG. 2. Similarly, notches 11R and 12R are formed at the right end 1RE and used to bend and raise the right end 1RE backward. A pair of the notches 11L and 11R is formed along the bend line BL1 and has a rectangular shape elongated in the right-left direction in a plan view. A pair of the notches 12L and 12R is formed along the bend line BL2 and has a V-shape in a plan view.

Note that among the notches 11L and 11R and the notches 12L and 12R constituted in pairs and not especially required to be separately described, only the portions of the notches 11R and 12R on one side will be given the reference numerals and dimensions but the reference numerals and dimensions of the portions of the notches 11L and 12L on the other side will be omitted to simplify the drawings.

The size of the notches 11L and 11R in the present embodiment is set so that their long side is preferably 10 to 25 mm, and that their short side is preferably 1 to 3 mm. In addition, a distance in the top-bottom direction from the upper end 1UE to an upper side 11LUS of the notch 11L is preferably 40 to 55 mm. Similarly, a distance from the upper end 1UE to an upper side 11RUS of the notch 11R is preferably 40 to 55 mm.

The size of the notches 12L and 12R is set so that a distance from an intersection point P1 of two straight lines constituting a V-shape to an opening bottom end P2 is preferably 10 mm as shown in FIG. 1. In addition, the opening length of the notches 12L and 12R is preferably 5 mm.

Note that as shown in FIG. 1, a bottom end 1DE is formed in a region R4 of the scrotal sheet 1. The bottom end 1DE has a rounded shape in a plan view. A distance in the top-bottom direction from the opening bottom end P2 to a most distant end 1MDE of the bottom end 1DE is preferably 15 to 40 mm.

(Layer Structure of Scrotal Sheet 1) Next, the layer structure of the scrotal sheet 1 will be described.

Figure 3:
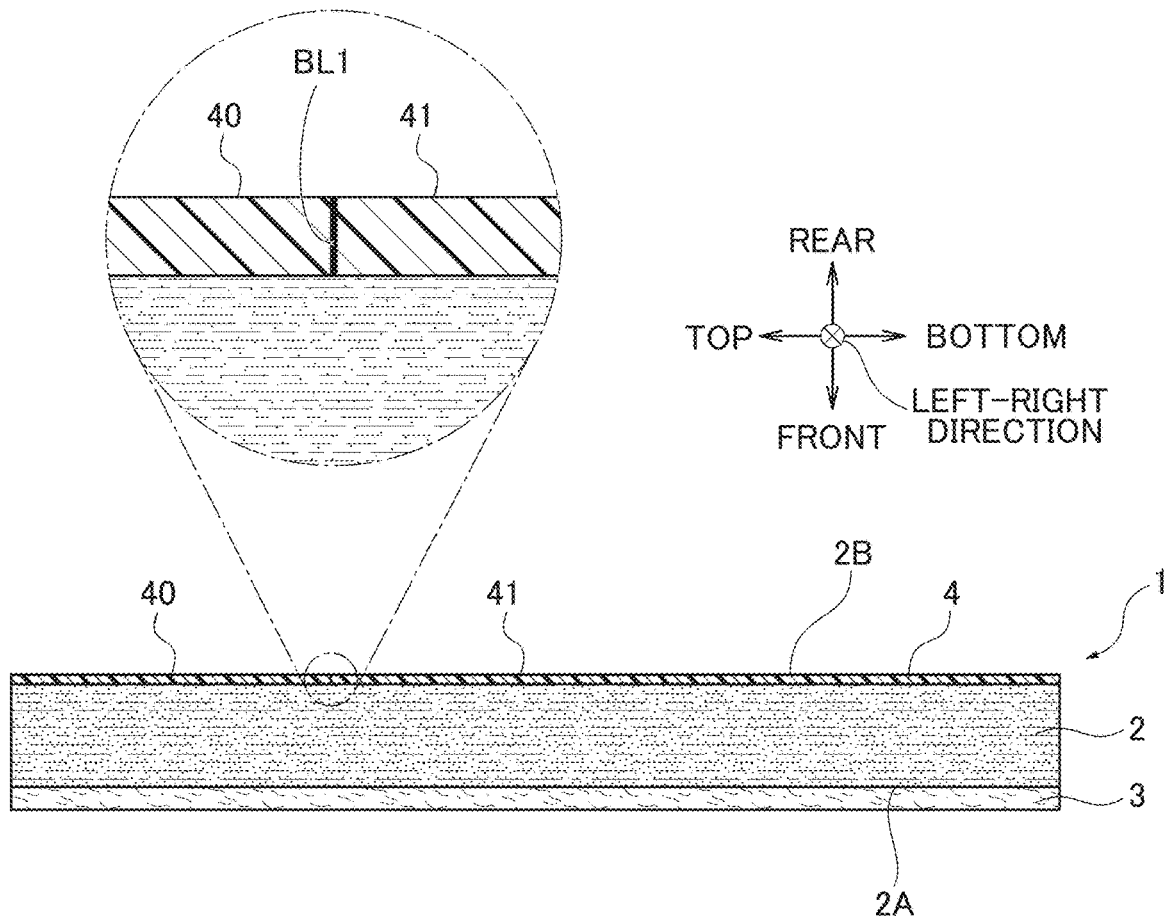
FIG. 3 is an enlarged view of a part of a cross section, viewed along arrows A-A in FIG. 1.

FIG. 3 is an enlarged view of a part of a cross section, viewed along arrows A-A in FIG. 1. As shown in FIG. 3, the scrotal sheet 1 includes a paste/water-retaining material layer 2, a surface material layer 3, and a surface protection film 4. The scrotal sheet 1 in the present embodiment has a triple-layer structure including the paste/water-retaining material layer 2, the surface protection film 4, and the surface material layer 3 interposed and arranged between the paste/water-retaining material layer 2 and the surface protection film 4.

(Configuration of Pate/Water-Retaining Material Layer 2) The paste/water-retaining material layer 2 contains at least moisture and a cooling material that uses the vaporization heat resulting from evaporation of the moisture.

From the viewpoint of keeping the scrotal sheet 1 clean, the paste/water-retaining material layer 2 preferably contains I-menthol that is significantly antibacterial as the cooling material.

In addition, from the viewpoint of realizing the scrotal sheet 1 that prevents skin inflammation, the content of the I-menthol is preferably 0.1 wt. % to 1.0 wt. % relative to the total weight of the moisture.

Moreover, from the viewpoint of realizing the scrotal sheet 1 that is significantly antibacterial, the weight of the paste/water-retaining material layer 2 is preferably 0.2 g to 0.4 g per 1 cm$^2$.

Further, from the viewpoint of giving a mental effect such as a relaxation feeling and a drowsiness shaking effect to a patient, the paste/water-retaining material layer 2 preferably contains an aromatic component selected from any one type of peppermint, basil, tea tree, eucalyptus, lemon, and blue gum.

Furthermore, from the viewpoint of reducing the possibility of growing mold or the like, the paste/water-retaining material layer 2 preferably contains an antiseptic agent made of paraben.

(Configuration of Surface Material Layer 3) The surface material layer 3 is made of an unwoven fabric in which fibers are irregularly connected to each other and formed on one surface 2A of the paste/water-retaining material layer 2.

(Configuration of Surface Protection Film 4) The surface protection film 4 is made of biocompatibility resin such as polyethylene, polypropylene, and polyimide. The surface protection film 4 is formed on the other surface 2B of the paste/water-retaining material layer 2. The surface 2B functions as an attachment surface 2B for the scrotum. As shown in an enlarged view of a portion surrounded by dashed lines in FIG. 3, the surface protection film 4 is divided into the plurality of portions 40 and 41 by the bend line BL1. By the bend line BL1, the surface protection film 4 is configured to be peelable from the other surface 2B of the paste/water-retaining material layer 2.

Figure 4:
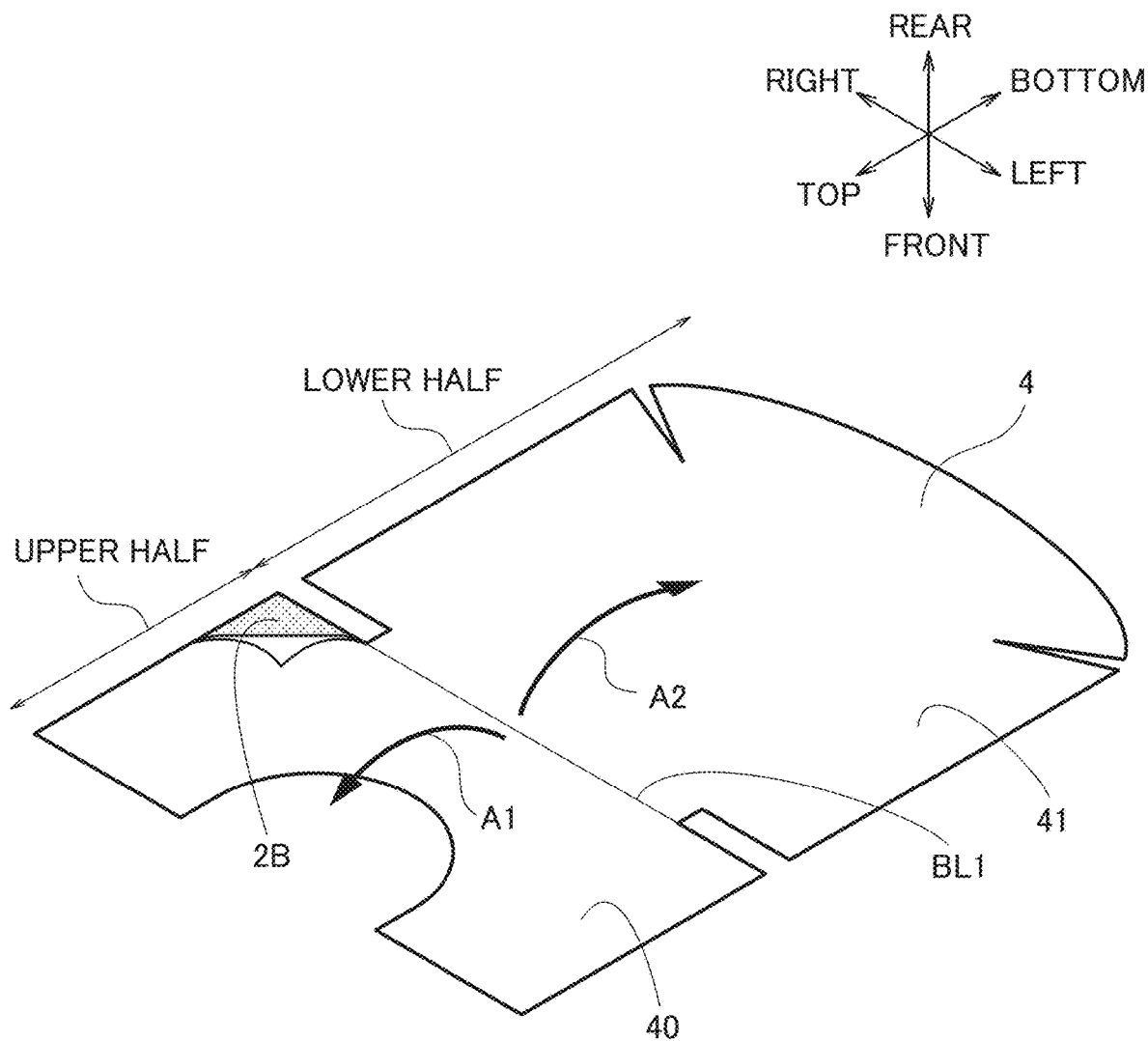
FIG. 4 is a view for describing an example of a procedure for attaching the scrotal sheet 1 according to a present embodiment.
Figure 5:
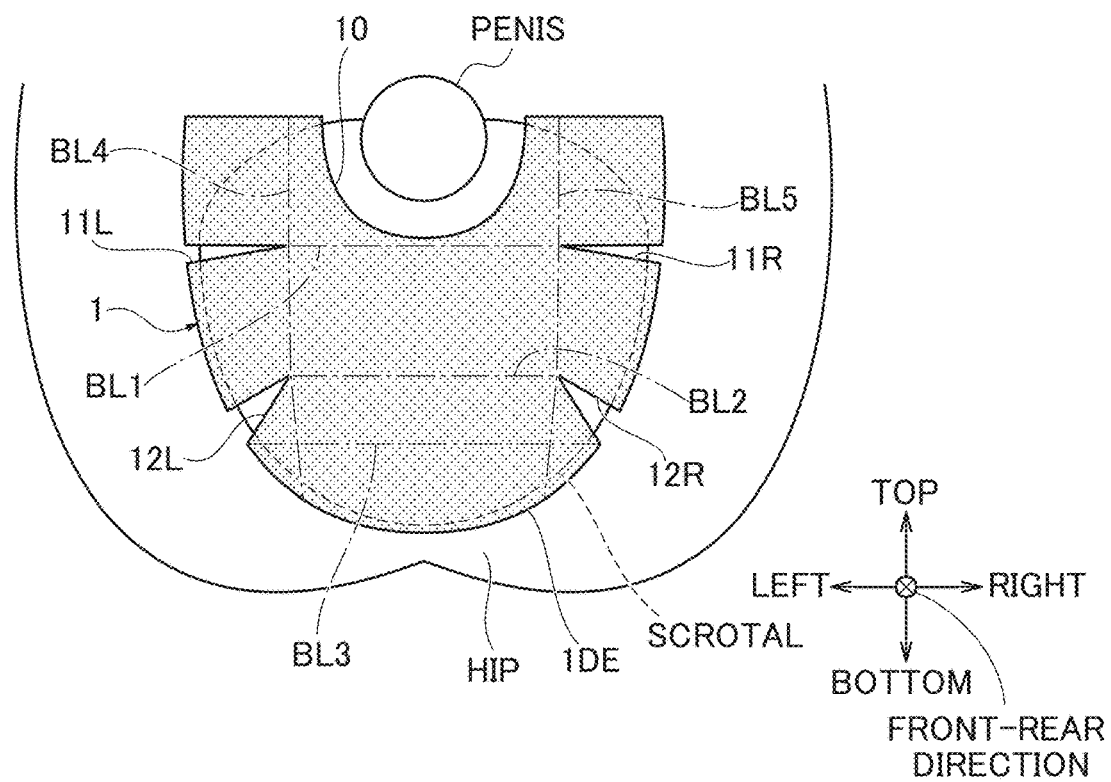
FIG. 5 is a view for describing the example of the procedure for attaching the scrotal sheet 1 according to the present embodiment.
Figure 6:
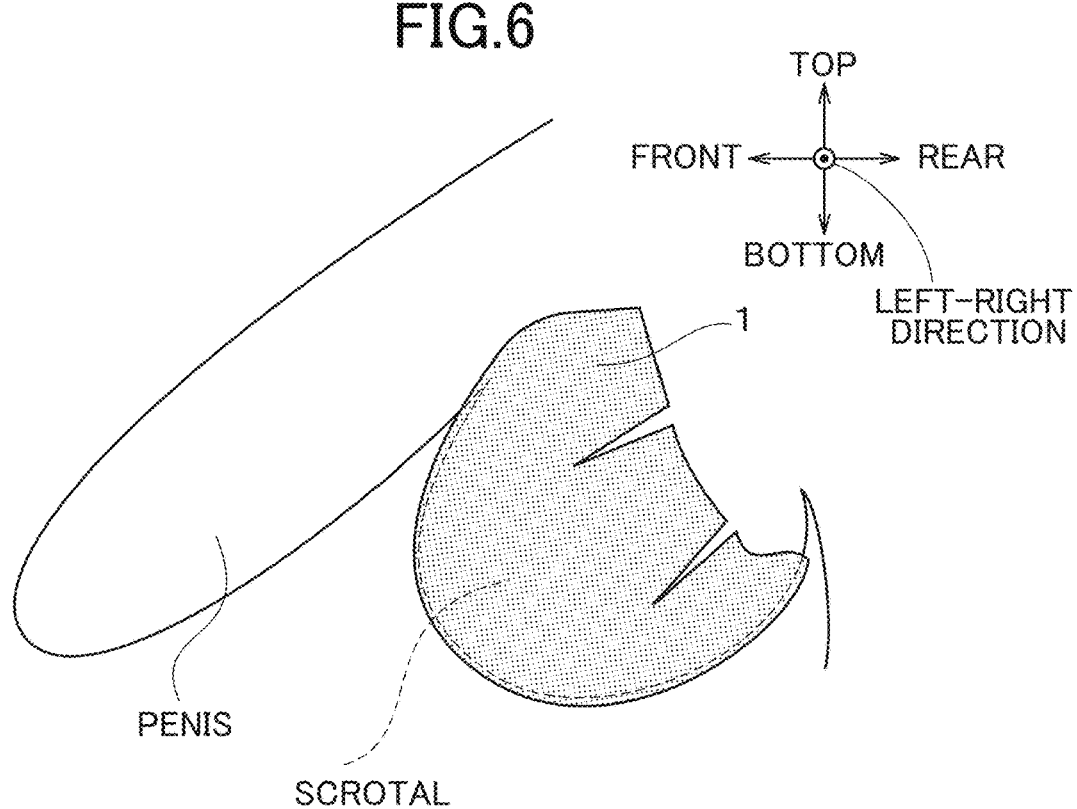
FIG. 6 is a view for describing the example of the procedure for attaching the scrotal sheet 1 according to the present embodiment.

(Procedure for Attaching Scrotal Sheet 1) FIGS. 4 to 6 are views for describing an example of a procedure for attaching the scrotal sheet according to the present embodiment.

FIG. 4 is a perspective view showing a state in which the surface protection film 4 attached to the paste/water-retaining material layer 2 is being peeled by half. In FIG. 4, the surface 2B is shown by hatching to facilitate the understanding of the figure.

FIG. 5 is a front view of the scrotal sheet attached to the groin. FIG. 6 is a side view of the scrotal sheet attached to the groin. In FIGS. 5 and 6, the scrotal sheet 1 is shown by hatching to facilitate the understanding of the figures.

At the time of attachment, a portion 40 is first peeled upward (in a direction shown by arrow A1 in the figure) as shown in FIG. 4. Here, only the portion 40 is peeled from the surface 2B to initially expose only the upper half of the surface 2B (the part above the bend line BL1 shown in FIG. 5) to an outside. Note that the notch 10 is formed at the upper half of the surface 2B.

Next, as shown in FIG. 5, the upper half (not shown) of the surface 2B is arranged to face the root portion of the penis so that the root portion of the penis is surrounded by the notch 10.

In this state, the upper half of the surface 2B is attached onto the skin of the facing root portion of the penis with the scrotal sheet 1 stretching in the right-left direction. Since the notch 10 has a semicircular shape in a plan view as shown in FIG. 1, the scrotal sheet 1 can cause the penis to be exposed to the outside and arranged at its central part in the right-left direction when attached to the groin.

Then, as shown in FIG. 4, the remaining portion 41 is peeled downward (in a direction shown by arrow A2 in FIG. 4). Here, the lower half of the surface 2B (the part below the bend line BL1 shown in FIG. 5) is also exposed to the outside as the remaining portion 41 is peeled, whereby the whole surface of surface 2B is exposed to the outside.

Next, the lower half of the surface 2B is arranged to face a portion of the scrotum lower than the root portion of the penis.

Then, the notches 11L, 11R, 12L, and 12R are expanded in a V-shape as shown in FIG. 5 with the scrotal sheet 1 stretching in the right-left direction and the bottom direction to appropriately adjust the fixation position of the lower half (not shown) of the surface 2B.

After the adjustment of the position, the scrotal sheet 1 is bent like mountains along the bend lines BL1 to BL5, and the lower half of the surface 2B is attached onto the skin of the facing portion of the scrotum. Thus, as shown in FIG. 6, the scrotal sheet 1 is attached to the portion of the scrotum.

Figure 7:
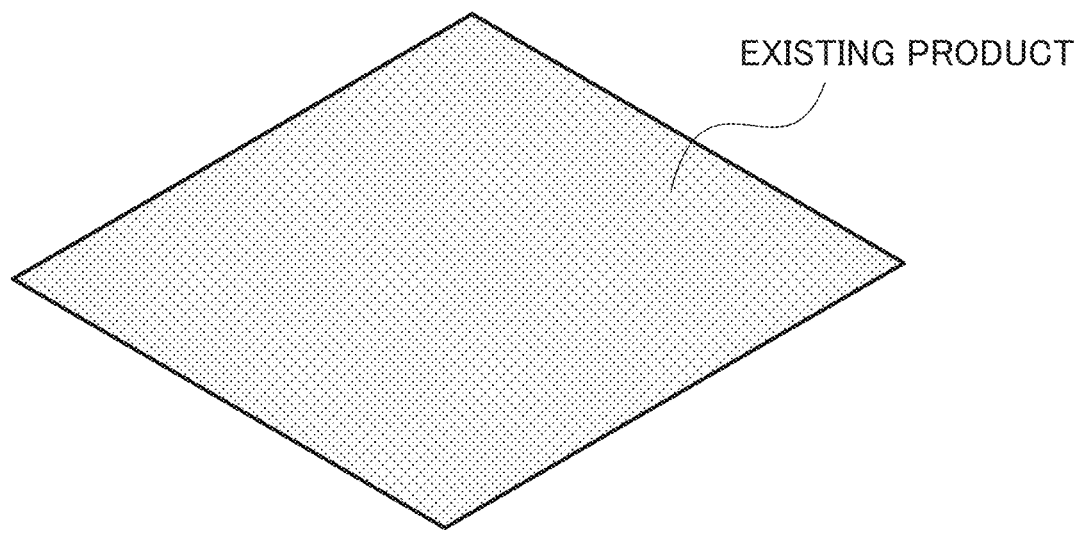
FIG. 7 is a perspective view of an existing product formed into a rectangular shape in a plan view.
Figure 8:
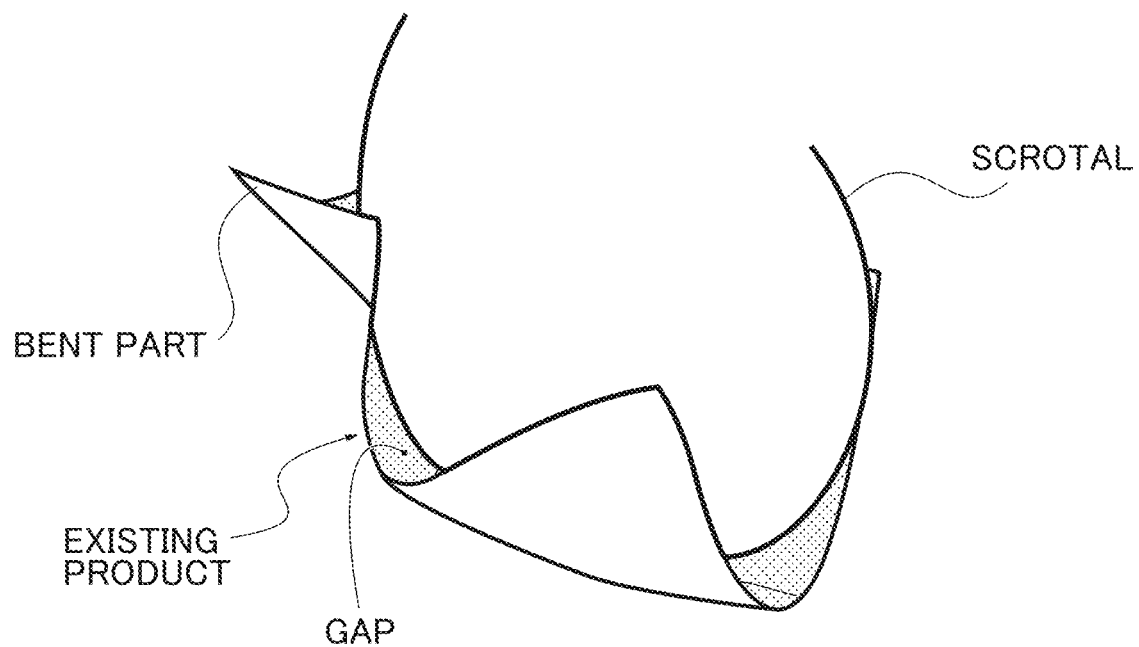
FIG. 8 is a perspective view showing a state in which the existing product is attached to the scrotum of a test subject.

Since the notches 11L and 11R have a rectangular shape in a plan view (see FIG. 1) as described above, the scrotal sheet 1 can produce an effect that the scrotal sheet 1 is easily attached to the scrotum and hardly peeled off when attached to the groin. In addition, the scrotal sheet 1 can be attached onto the skin of a desired portion during use to obtain, for example, a sustainable cool feeling in the scrotum. Here, FIG. 7 is a perspective view of an existing product formed into a rectangular shape in a plan view. In addition, FIG. 8 is a perspective view showing a state in which the existing product is attached to the scrotum of a test subject. As shown in FIG. 7, the existing product is angulated at its four corners in a plan view. Therefore, as shown in FIG. 8, when the existing product is attached to the scrotum, a gap is formed between the existing product and the scrotum or bent parts formed at the four corners contact an underwear (not shown). Accordingly, since the existing product is easily peeled off from the scrotum and poorly adheres to the scrotum, the existing product is not suitable for attachment to the scrotum.

Since the notches 12L and 12R have a V-shape in a plan view as described above (see FIG. 1), the downward and backward stretching of the scrotal sheet 1 is promoted, which can produce an effect that the scrotal sheet 1 is easily attached to the scrotum and hardly peeled off from the scrotum and can realize the flexible and smooth positioning of the scrotal sheet 1 with respect to a target attachment portion.

Since the bottom end 1DE of the region R4 is rounded in a plan view as described above (see FIG. 1), the bottom end 1DE functions as a cushioning material that absorbs an impact when contacting the hip and can produce an effect that the hip are prevented from being damaged or injured even if the bottom end 1DE contacts the hip or the hip is free from pain even if the bottom end 1DE contacts the hip.

The embodiments of the present disclosure are described above based on the drawings. However, needless to say, specific configurations are not limited to these embodiments. The scope of the present disclosure is not shown in the description of the above embodiments but is shown in claims. In addition, all modifications within a similar range are included without departing from the claims.

Note that the above embodiments describe an example in which the notch 10 has a semicircular shape in a plan view. The shape of the notch 10 is not limited to this shape, but the notch 10 can be formed into various shapes such as a semi-elliptic shape and a rectangular shape so long as the scrotum is easily surrounded. In addition, the number of the notch 10 is not limited to one but may be two or more.

Similarly, the above embodiments describe an example in which the notches 11L and 11R have a rectangular shape elongated in the right-left direction in a plan view. The shape of the notches 11L and 11R is not limited to this shape, but the notches 11L and 11R can be formed into various shapes so long as the scrotum is easily surrounded. In addition, the number of the notches 11L and 11R is not limited to two and may be one or three or more.

Similarly, the above embodiments describe an example in which the notches 12L and 12R have a V-shape in a plan view. The shape of the notches 12L and 12R is not limited to this shape, but the notches 12L and 12R can be formed into various shapes so long as the scrotum is easily surrounded. In addition, the number of the notches 12L and 12R is not limited to two and may be one or three or more.

Embodiments

Next, the present disclosure will be described in detail using an exemplary embodiment. Note that the present disclosure is not limited to the following example.

Here, experimental results using a thermography as to whether the temperature of the scrotum can be cooled by the attachment of the scrotal cooling sheet will be described.

Figure 9:
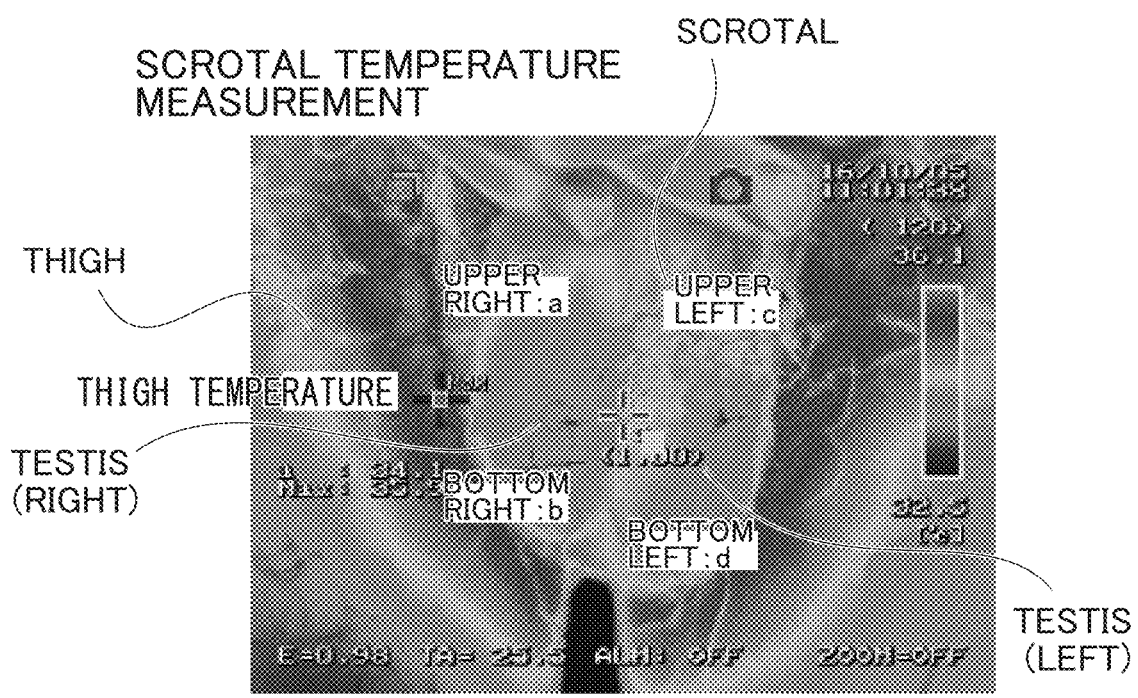
FIG. 9 is a photograph showing a change in surface temperature of the scrotum when a scrotal cooling sheet is attached to the scrotum.

Experimental subjects and an experimental method will be described below. In addition, a photograph showing a change in surface temperature of the scrotum when the scrotal cooling sheet was attached is shown in FIG. 9.

(Experimental Subjects) Here, test subjects were 26 healthy young males ranging from 19 to 22 years old.

(Experimental Method) Here, the cooling effect of the scrotal cooling sheet was examined by the comparison between the temperature of the scrotum and the temperature of the thighs.

First, before the attachment of the scrotal cooling sheet, the surface temperature of the scrotum was measured using a thermography (InfReC R300SR (product name) manufactured by Nippon Avionics Co., Ltd.). Then, the scrotal cooling sheet was peeled off in one hour, two hours, and four hours after the attachment, and then the temperature of the scrotum was measured. FIG. 9 is the photograph showing the change in the surface temperature of the scrotum when the scrotal cooling sheet was attached. As shown in FIG. 9, in this experiment, the temperatures of the four points of the scrotum were measured, and the effect of cooling the scrotum was examined by the comparison between the measured temperatures and the temperature of the thighs. Specifically, as shown in FIG. 9, the temperatures of an upper right point a, a bottom right point b, an upper left point c, and a bottom left point d of the testes and the temperature of the thighs were measured.

Figure 10:
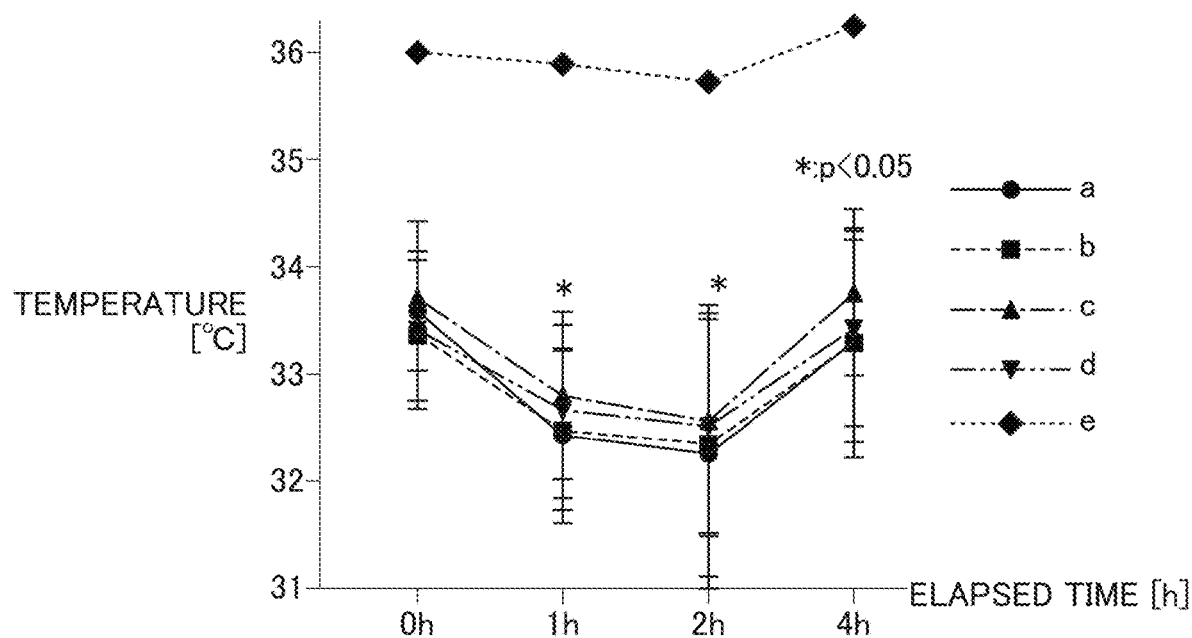
FIG. 10 is a graph showing the relationship between the temperature of the scrotum and the temperature of thighs.

(Relationship between Temperature of Scrotum and Temperature of Thighs) FIG. 10 is a graph showing the relationship between the temperature of the scrotum and the temperature of the thighs. In FIG. 10, a horizontal axis shows an elapsed time [h] after the attachment of the scrotal cooling sheet, and a vertical axis shows a temperature [° C.]. In FIG. 10, "●" shows the average temperature of the upper right point a (see FIG. 9) of the testes of the test subjects, and "■" shows the average temperature of the bottom right point b (see FIG. 9) of the testes of the test subjects. In addition, in FIG. 10, "▲" shows the average temperature of the upper left point c (see FIG. 9) of the testes of the test subjects, and "▼" shows the average temperature of the bottom left point d (see FIG. 9) of the testes of the test subjects. In FIG. 10, "◆" shows the average temperature of the thighs (see FIG. 9) of the test subjects.

In FIG. 10, "*" shows that the significant difference between the temperature of the scrotum in zero hours (0[h]) after which the attachment of the scrotal cooling sheet was started and in 4[h] after the attachment of the scrotal cooling sheet and the temperature of the scrotum in 1[h] and 2[h] after the attachment of the scrotal cooling sheet was admitted at a significant level $p<0.05$. Here, the "significant level p" represents a "level at which the difference is statistically meaningful," and represents that the difference hardly occurs by chance when p has a smaller value.

From the examination of FIG. 10, it was found that the temperature of the scrotum at each of the points a to d was distributed in the temperature range of 33° C. to 34° C. in 0[h] after which the attachment of the scrotal cooling sheet was started and in 4[h] after the attachment of the scrotal cooling sheet.

In addition, from the examination of FIG. 10, it was found that the temperature of the scrotum at each of the points a to d was distributed in the temperature range of 32° C. to 33° C. in 1[h] and 2[h] after the attachment of the scrotal cooling sheet.

From these examination results, it was found that the temperature of the scrotum at each of the points a to d was significantly lower, and a higher cooling effect was produced in 1[h] and 2[h] after the attachment, compared with those in 0[h] after which the attachment of the scrotal cooling sheet was started and in 4[h] after the attachment of the scrotal cooling sheet.

On the other hand, it was found that the temperature of the thighs was distributed near 36° C. in 0[h] after which the attachment of the scrotal cooling sheet was started and in 1[h], 2[h], and 4[h] after the attachment of the scrotal cooling sheet.

Figure 11:
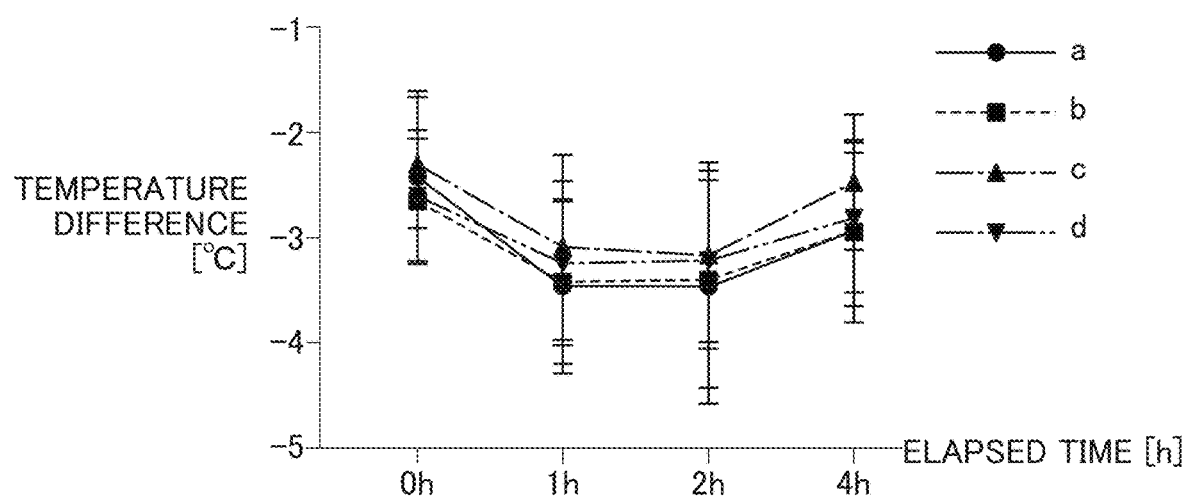
FIG. 11 is a graph showing a difference in temperature between the temperature of the scrotum and the temperature of the thighs.

(Comparison of Difference in Temperature between Temperature of Scrotum and Temperature of Thighs) FIG. 11 is a graph showing a difference in temperature between the temperature of the scrotum and the temperature of the thighs. In FIG. 11, a horizontal axis shows an elapsed time [h] after the attachment of the scrotal cooling sheet, and a vertical axis shows a difference in temperature between the temperature of the scrotum and the temperature of the thigh. In FIG. 11, "●" shows a difference in temperature [° C.] between the average temperature of the upper right point a (see FIG. 9) of the testes of the test subjects and the average temperature of the thighs (see FIG. 9) of the test subjects. In FIG. 11, "■" shows a difference in temperature [° C.] between the average temperature of the bottom right point b (see FIG. 9) of the testes of the test subjects and the average temperature of the thighs (see FIG. 9) of the test subjects. In FIG. 11, "▲" shows a difference in temperature [° C.] between the average temperature of the upper left point c (see FIG. 9) of the testes of the test subjects and the average temperature of the thighs (see FIG. 9) of the test subjects. In FIG. 11, "▼" shows a difference in temperature [° C.] between the average temperature of the bottom left point d (see FIG. 9) of the testes of the test subjects and the average temperature of the thighs (see FIG. 9) of the test subjects.

From the examination of FIG. 11, it was found that the difference in temperature between the temperature of the scrotum at each of the points a to d and the temperature of the thighs was distributed in the temperature range of −3° C. to −2° C. in 0[h] after which the attachment of the scrotal cooling sheet was started and in 4[h] after the attachment of the scrotal cooling sheet.

In addition, from the examination of FIG. 11, it was found that the difference in temperature between the temperature of the scrotum at each of the points a to d and the temperature of the thighs was distributed in the temperature range of about −3.5° C. to −3° C. in 1[h] and 2[h] after the attachment of the scrotal cooling sheet.

From these examination results, it was found that the difference in temperature between the temperature of the scrotum at each of the points a to d and the temperature of the thighs was significantly higher in 1[h] and 2[h] after the attachment than in 0[h] after which the attachment was started and in 4[h] after the attachment, and that a higher cooling effect was produced.

(Wearing Comfort and Presence or Absence of Itchiness after Attachment) In the experiment, the present inventors also examined wearing comfort and the presence or absence of itchiness after the attachment of the scrotal cooling sheet.

(Wearing Comfort) The following Table 1 shows results obtained when the 26 test subjects had the scrotal cooling sheet attached thereto and evaluated wearing comfort based on a scoring reference using "very good," "good," "average," "bad," and "very bad."

TABLE 1

| <WEARING COMFORT> | | | | |
| --- | --- | --- | --- | --- |
| VERY GOOD | GOOD | AVERAGE | BAD | VERY BAD |
| 2 | 9 | 14 | 1 | 0 |

As shown in Table 1, two of the 26 test subjects evaluated the wearing comfort as being "very good." Nine test subjects evaluated the wearing comfort as being "good." 14 test subjects evaluated the wearing comfort as being "average."

On the other hand, as shown in FIG. 1, one of the 26 test subjects evaluated the wearing comfort as being "bad." Note that none of the 26 test subjects evaluated the wearing comfort as being "very bad."

From these examination results, it was found that the 25 test subjects evaluated the wearing comfort of the scrotal cooling sheet as being "very good," "good," or "average" and were considerably greater in number than the one test subject who evaluated the wearing comfort as being "bad."

(Presence or Absence of Itchiness) The following Table 2 shows results obtained when the 26 test subjects had the scrotal cooling sheet attached thereto and evaluated the presence or absence of itchiness when the scrotal cooling sheet was attached based on a scoring reference using "slightly itching" and "none."

TABLE 2

| <ITCHINESS> | |
| --- | --- |
| SLIGHTLY ITCHING | NONE |
| 1 | 25 |

As shown in Table 2, one of the 26 test subjects evaluated the presence or absence of itchiness as being "slightly itching." On the other hand, the remaining 25 test subjects evaluated the presence or absence of itchiness as being "none."

From these examination results, it was found that only the one test subject evaluated the presence or absence of itchiness as being "slightly itching" while the remaining 25 test subjects evaluated the presence or absence of itchiness as being "none" when the scrotal cooling sheet was attached, and most of the test subjects did not feel itchiness.

REFERENCE SIGNS LIST

1 Scrotal sheet, 2 Paste/water-retaining material layer, 2A, 2B Surface, 3 Surface material layer, 4 Surface protection film, 10, 11L, 11R, 12L, 12R Notch

The invention claimed is:

1. A scrotal sheet for cooling a scrotum, the scrotal sheet having an elongated shape elongated in one longitudinal direction as a whole, the scrotal sheet comprising:
   a first longitudinal end;
   a second longitudinal end opposite to the first longitudinal end in the longitudinal direction;
   a pair of side ends perpendicular to the first longitudinal end;
   a paste/water-retaining material layer comprising at least moisture and a cooling material that uses vaporization heat resulting from evaporation of the moisture;
   a surface material layer on a surface of the paste/water-retaining material layer;
   first cutouts configured to form a three-dimensional shape to surround the scrotum when the scrotal sheet is used;
   a second cutout formed semicircular at a center of the first longitudinal end of the scrotal sheet and extending toward the second longitudinal end adapted to surround a root portion of a penis;
   a plurality of transverse bend lines parallel to the first longitudinal end, the plurality of transverse bend lines configured to divide the scrotal sheet into a plurality of longitudinal portions; and
   a pair of longitudinal bend lines respectively extending along the side ends of the scrotal sheet and perpendicular to the plurality of transverse bend lines, the pair of longitudinal bend lines configured to divide the scrotal sheet into three transverse portions,
   wherein the plurality of transverse bend lines comprises:
   a first transverse bend line, and
   a second transverse bend line between the first longitudinal end and the first transverse bend line,
   wherein the first cutouts comprise:
   rectangular cutouts at both ends of the second transverse bend line, the rectangular cutouts extending inwardly from the side ends of the scrotal sheet; and
   V-shaped cutouts at both ends of the first transverse bend line,
   wherein two outer transverse portions of the three transverse portions divided by the pair of longitudinal bend lines are further divided by the rectangular cutouts and the V-shaped cutouts, respectively.

2. The scrotal sheet according to claim 1, wherein at least one of the first cutouts is formed at each end of the scrotal sheet perpendicular to the first longitudinal end and configured to bend and raise the each end.

3. The scrotal sheet according to claim 1, further comprising
   a surface protection film on another surface of the paste/water-retaining material layer, the surface protection film divided into a plurality of portions, and
   wherein the surface protection film is configured to be peelable along the second transverse bend line.

4. The scrotal sheet according to claim 2, further comprising
   a surface protection film on another surface of the paste/water-retaining material layer, the surface protection film divided into a plurality of portions.

5. The scrotal sheet according to claim 1, wherein the scrotal sheet is self-adhering sheet.

6. The scrotal sheet according to claim 1, wherein the second longitudinal end of the scrotal sheet comprises a rounded shape in a plan view.

7. The scrotal sheet according to claim 1, wherein
   the second transverse bend line extends continuously with an upper side of the rectangular cutouts, and
   wherein the first and second transverse bend lines and the pair of longitudinal bend lines intersect each other at inner ends of the upper side of the rectangular cutouts and at inner ends of the V-shaped cutouts.

8. The scrotal sheet according to claim 1, wherein the paste/water-retaining material layer continuously extends over an entire area of the scrotal sheet in a plan view.

* * * * *